US011619584B2

(12) United States Patent
Wang et al.

(10) Patent No.: US 11,619,584 B2
(45) Date of Patent: Apr. 4, 2023

(54) TIME-RESOLVED FLUORESCENCE IMMUNOCHROMATOGRAPHIC TEST PAPER CARD FOR TESTING CLOTHIANIDIN

(71) Applicant: Tobacco Research Institute of Chinese Academy of Agricultural Sciences, Qingdao (CN)

(72) Inventors: Xiuguo Wang, Qingdao (CN); Xiao Zhang, Qingdao (CN); Qing Guo, Qingdao (CN)

(73) Assignee: TOBACCO RESEARCH INSTITUTE OF CHINESE ACADEMY OF AGRICULTURAL SCIENCES, Qingdao (CN)

(*) Notice: Subject to any disclaimer, the term of this patent is extended or adjusted under 35 U.S.C. 154(b) by 321 days.

(21) Appl. No.: 16/924,890

(22) Filed: Jul. 9, 2020

(65) Prior Publication Data
US 2021/0278344 A1 Sep. 9, 2021

(30) Foreign Application Priority Data
Mar. 9, 2020 (CN) .......................... 202010158854.8

(51) Int. Cl.
*G01N 21/64* (2006.01)
*G01N 33/543* (2006.01)
(Continued)

(52) U.S. Cl.
CPC ....... *G01N 21/6408* (2013.01); *G01N 21/643* (2013.01); *G01N 21/8483* (2013.01);
(Continued)

(58) Field of Classification Search
CPC .... B01D 67/0088; B01D 71/56; B01D 71/80; C08G 69/40; C08G 69/48;
(Continued)

(56) References Cited

U.S. PATENT DOCUMENTS

2018/0141040 A1* 5/2018 Strong ............. G01N 33/54386

OTHER PUBLICATIONS

-Tsai, T-T, Huang, T-H, Chen, C-A, Ho, N Yi-Ju & Chen, C-F. Development a stacking pad design for enhancing the sensitivity of lateral flow immunoassay. Nat. Scientific Reports. 8:17319 (2018) (Year: 2018).*

(Continued)

*Primary Examiner* — Christopher L Chin
*Assistant Examiner* — Estifanos Hailu

(57) ABSTRACT

A time-resolved fluorescence immunochromatographic test paper card for testing clothianidin. A binding pad includes a detection microsphere and a quality control microsphere thereon, wherein the detection microsphere is a fluorescent microsphere coated with a clothianidin monoclonal antibody on the surface thereof, the quality control microsphere is a fluorescent microsphere coated with a rabbit anti-tag protein on the surface thereof. An NC film is provided with a detection line and a control line. The lengths of the detection line and the control line are the same as the width of the NC film. A first clamping part is arranged at one end of the sample pad. A second clamping part and a third clamping part are respectively arranged at two ends of the binding pad. A fourth clamping part is arranged at one end of the NC film, the other end of the NC film is joined with an absorption pad.

7 Claims, 1 Drawing Sheet

(51) Int. Cl.
   *G01N 21/84*    (2006.01)
   *G01N 33/533*   (2006.01)
   *G01N 33/53*    (2006.01)
   *G01N 33/558*   (2006.01)

(52) U.S. Cl.
   CPC ....... *G01N 33/533* (2013.01); *G01N 33/5308* (2013.01); *G01N 33/54386* (2013.01); *G01N 33/54388* (2021.08); *G01N 33/558* (2013.01); *G01N 2430/10* (2013.01)

(58) Field of Classification Search
   CPC ....... G01N 2021/7786; G01N 21/6408; G01N 21/643; G01N 21/8483; G01N 2430/10; G01N 33/5308; G01N 33/533; G01N 33/54386; G01N 33/54388; G01N 33/558; G01N 33/54387; G01N 33/54389
   USPC ...... 435/7.1, 287.9, 970, 805, 810; 436/169, 436/170, 514, 518, 530, 810; 422/400, 422/401, 420, 421, 425, 426, 430
   See application file for complete search history.

(56) References Cited

OTHER PUBLICATIONS

-Li, M, Hua, X, Ma, M, Liu, J, Zhou, L & Wang, M. Detecting clothianidin residues in environmental and agricultural samples using rapid, sensitive enzye-linked immunosorbent assay and gold immunochromatographic assay. Science of the Total Environment. 499 1-6 (2014). (Year: 2014).*

* cited by examiner ized on the base plate. The binding pad includes a detection micro-
TIME-RESOLVED FLUORESCENCE IMMUNOCHROMATOGRAPHIC TEST PAPER CARD FOR TESTING CLOTHIANIDIN This application claims the benefit of Chinese Patent Application No. 202010158854.8, filed Mar. 9, 2020, which is hereby incorporated by reference in its entirety.

FIELD

The present invention belongs to the field of clothianidin detection, and particularly relates to a time-resolved fluorescence immunochromatographic test paper card for testing clothianidin.

BACKGROUND

Clothianidin is a high-efficiency and safe new pesticide with contact killing, stomach toxicity and systemic activities. The clothianidin is mainly used for controlling hemiptera, coleoptera, diptera and certain orders of pests on crops, and has excellent systemic activity and permeation effect, which is superior to traditional nicotine insecticides. As people pay more and more attention to health problems, the detection of pesticide residues is becoming a hot spot. Traditional clothianidin detection is mostly conducted by chromatography. However, although such a detection method is accurate, it is complicated in pretreatment, resulting in high cost and long time of the detection, which cannot meet the requirements of rapid detection of a large number of samples.

In view of the shortcomings of the prior art, a time-resolved fluorescence immunochromatographic test paper card for testing the clothianidin is needed to improve the detection efficiency of the sample on the premise of ensuring the detection sensitivity.

SUMMARY

An objective of the present invention is to provide a time-resolved fluorescence immunochromatographic test paper card for testing clothianidin, which improves the absorption speed and diffusion speed of a sample, and improves the detection sensitivity and the detection efficiency.

The present invention provides the following technical solutions:

A time-resolved fluorescence immunochromatographic test paper card for testing clothianidin, including a base plate, and a sample pad, a binding pad, an Nitrocellulose NC film and an absorption pad that are sequentially arranged on the base plate. The binding pad includes a detection microsphere and a quality control microsphere thereon, wherein the detection microsphere is a fluorescent microsphere coated with a clothianidin monoclonal antibody on the surface thereof, and the quality control microsphere is a fluorescent microsphere coated with a rabbit anti-tag protein on the surface thereof. The NC film is provided with a detection line and a control line thereon, the lengths of the detection line and the control line are the same as the width of the NC film, the detection line is coated with a clothianidin antigen thereon, and the quality control line is coated with an anti-rabbit antibody thereon. A first clamping part is arranged at one end of the sample pad. A second clamping part and a third clamping part are respectively arranged at two ends of the binding pad. A fourth clamping part is arranged at one end of the NC film, and the other end of the NC film is joined with the absorption pad. The first clamping part, the second clamping part, the third clamping part and the fourth clamping part are all of semi-arc structures. The first clamping part and the second clamping part fit to each other, and the third clamping part and the fourth clamping part fit to each other. The binding area between the sample pad and the binding pad and the binding area between the binding pad and the NC film are improved through the semi-arc clamping parts, so that the diffusion speed of the sample can be greatly improved, and further the detection efficiency and sensitivity can be effectively improved. Through mutual engaging of the semi-arc clamping parts, the structural stability of the test paper card can be improved, and the reliability of product quality is ensured.

Preferably, the upper side surface of the other end of the sample pad is provided with several groove-shaped structures, as shown in FIG. 1, so that the diffusion contact area of the sample can be greatly increased, the diffusion speed of the sample can be accelerated, and in turn the absorption speed can be increased, which is conducive to improve the detection efficiency and sensitivity.

Preferably, the first clamping portion and the sample pad; the second clamping part, the third clamping part and the bonding pad; and the fourth clamping part and the NC film are all integrally formed structures, and the integrally formed structures are firm and stable in binding.

Preferably, the base plate is provided with a first semi-arc supporting part and a second semi-arc supporting part thereon. The first supporting part is positioned at the lower side of the second clamping part. The second supporting part is positioned at the lower side of the third clamping part. The stability of the clamping parts can be improved through the supporting effect of the supporting parts;

Preferably, the joint portion between the NC film and the absorbent pad is corrugated. That is, a concave-convex alternate structure is presented on an end surface of the NC film; a concave-convex alternate structure is presented on an end surface of the absorption pad; and the NC film and the absorption pad are embedded and engaged with each other. Such a structure can greatly improve the diffusion speed of the sample, thereby effectively improving the detection efficiency and sensitivity. Through mutual engaging of the semi-arc clamping parts, the structural stability of the test paper card can be improved, and the reliability of product quality is ensured.

Preferably, a raised buffer part is arranged in the middle of the absorbent pad, a third supporting part is arranged on the base plate below the buffer part, and the third supporting part plays a supporting role to improve the structural stability of the device.

Preferably, the fitting parts of the first clamping part the second clamping part, the third clamping part and the fourth clamping part are engaged into each other through the concave-convex alternate structure, which can increase the contact area in addition to ensuring the stability of the engagement, thereby facilitating the acceleration of the diffusion speed, and thus facilitating the improvement of the detection efficiency.

Preferably, the upper side surface of the second clamping part is provided with a projection, and the width of the projection is smaller than the width of the second clamping part, so that the engaging stability can be ensured and the contact area can be increased. The lower side surface of the first clamping part is provided with a strip-shaped groove. The protrusion is embedded in the groove, so that the contact area of the sample can be increased, the absorption speed can be further increased, and the diffusion speed of the sample can be greatly increased.

Advantageous Effects of Invention

According to the present invention, by improving the binding area between the sample pad and the binding pad and the binding area between the binding pad and the NC film, the diffusion speed of the sample can be greatly improved, thereby effectively improving the detection efficiency and sensitivity; and through the structure of the clamping parts, the structural stability of the test paper card can be improved, and the reliability of the product quality is ensured.

BRIEF DESCRIPTION OF THE DRAWINGS

The accompanying drawings are used to provide further understanding of the present invention and constitute a part of the specification. The accompanying drawings, together with the examples of the present invention, are used to explain the present invention but do not pose a limitation to the present invention. In the accompanying drawings.

The reference symbols are: 1. base plate; 2. sample pad; 3. binding pad; 4. NC film; 5. absorption pad; 6. the first clamping part; 7. the second clamping part; 8. the third clamping part; 9. the fourth clamping part; 10. detection line; 11, quality control line; 12. buffer part; 13. the first supporting part; 14. the second supporting part; and 15. the third supporting part.

DETAILED DESCRIPTION

Figure 1:
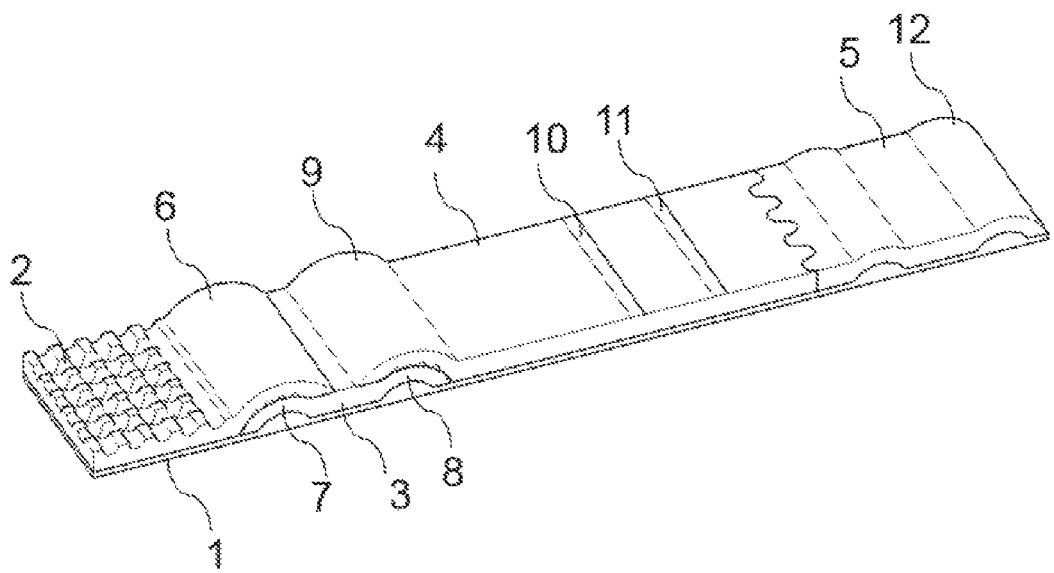
FIG. 1 is a front view of that present invention.
Figure 2:
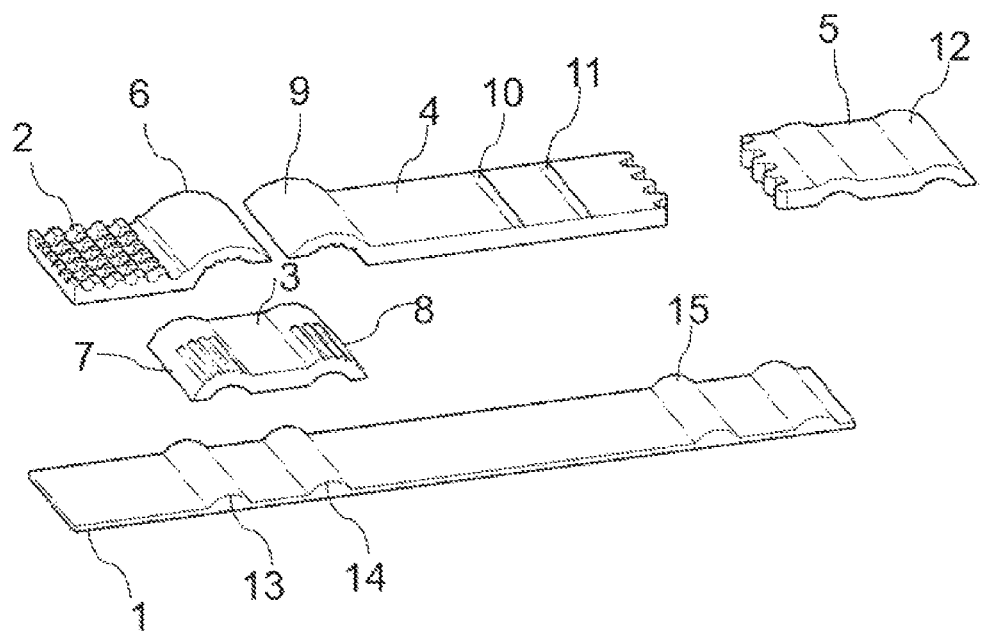
FIG. 2 is an exploded structure view of the present invention.

As shown in FIGS. 1 and 2, a time-resolved fluorescence immunochromatographic test paper card for testing clothianidin includes a base plate 1, and a sample pad 2, a binding pad 3, an NC film 4 and an absorption pad 5 which are sequentially arranged on the base plate 1. The binding pad 3 includes a detection microsphere and a quality control microsphere, wherein the detection microsphere is a fluorescent microsphere coated with a clothianidin monoclonal antibody on the surface thereof, and the quality control microsphere is a fluorescent microsphere coated with a rabbit anti-tag protein on the surface thereof. The NC membrane 4 is provided with a detection line 10 and a control line 11. The lengths of the detection line 10 and the control line 11 are the same as the width of the NC film 4. The detection line 10 is coated with a clothianidin antigen. The quality control line 11 is coated with an anti-rabbit antibody. A first clamping part 6 for clamping is arranged at one end of that sample pad 2. A second clamping part 7 and a third clamping part 8 for clamping are respectively arranged at two ends of the binding pad 3. A fourth clamping part 9 for clamping is arranged at one end of the NC film 4, and the other end of the NC film 4 is joined with the absorption pad 5. The first clamping part 6, the second clamping part 7, the third clamping part 8 and the fourth clamping part 9 are all of semi-arc structures. The arc-shaped structures can ensure better, more convenient and accurate joint among the first clamping part 6, the second clamping part 7, the third clamping part 8 and the fourth clamping part 9.

The first clamping part 6 and the second clamping part 7 are fit to each other, and the third holding part 8 and the fourth holding part 9 fit to each other. The binding area between the sample pad 2 and the binding pad 3 and the binding area between the binding pad 3 and the NC film 4 are improved through the semi-arc clamping parts, so that the diffusion speed of the sample can be greatly improved, thereby effectively improving the detection efficiency and sensitivity; and through mutual engaging of the semi-arc clamping parts, the structural stability of the test paper card can be improved, and the reliability of product quality is ensured.

The upper side surface of the other end of the sample pad 2 is provided with several groove-shaped structures, as shown in FIG. 1, so that the diffusion contact area of the sample can be greatly increased, the diffusion speed of the sample can be accelerated, and in turn the absorption speed can be increased, which is conducive to improve the detection efficiency and sensitivity. The first clamping part 6 and the sample pad 2; the second clamping part 7, the third clamping part 8 and the bonding pad 3; and the fourth clamping part 9 and the NC film 4 are all integrally formed structures, so that the toughness and service life of the device can be improved. The base plate 1 is provided with a first semi-arc supporting part 13 and a second semi-arc supporting part 14. The first supporting part 13 is located at the lower side of the second clamping part 7. The second supporting part 14 is located at the lower side of the third clamping part 8. Through the supporting parts, the supporting stability can be improved, which is beneficial for improving the reliability of the device. The joint portion between the NC film 4 and the absorbent pad 5 is corrugated. That is, a concave-convex alternate structure is presented on an end surface of the NC film 4; a concave-convex alternate structure is presented on an end surface of the absorption pad 5 has a structure of alternate concavities and convexities; and the NC film 4 and the absorbent pad 5 are embedded and engaged with each other. A raised buffer part 12 is arranged in the middle of the absorbent pad 5, and a third supporting part 15 is arranged on the base plate 1 below the buffer part 12. The third supporting part 15 can improve the structural stability. The fitting parts of the first clamping part 6, the second clamping part 7, the third clamping part 8 and the fourth clamping part 9 are engaged into each other through the concave-convex alternate structure. Such a structure can improve the absorption contact area of the sample, thereby improving the absorption speed and the diffusion speed. The upper side surface of the second clamping part 7 is provided with a projection, and the width of the projection is smaller than the width of the second clamping part 7, thereby ensuring the structural stability of the whole clamping part. The low side surface of the first clamping part 6 is provided with a strip-shaped groove; the projection is embedded in the groove; such that the contact area of the sample can be increased, and thus the absorption speed is improved, which can greatly improve the diffusion speed of the sample.

The present invention has the advantages that the binding area between the sample pad 2 and the binding pad 3 and the binding area between the binding pad 3 and the NC film 4 are improved through the semi-arc clamping parts, so that the diffusion speed of the sample can be greatly improved, thereby effectively improving the detection efficiency and sensitivity; and through mutual engaging of the semi-arc clamping parts, the structural stability of the test paper card can be improved, and the reliability of product quality is ensured.

It should be noted that the above descriptions are only preferred examples of the present invention and are not intended to limit the present invention. Although the present invention is described in detail with reference to the foregoing examples, a person skilled in the art can still make modifications to the technical solutions described in the foregoing examples, or make equivalent replacement to some technical characteristics. Any modifications, equivalent substitutions, improvements, etc. made within the spirit and scope of the present invention should be included within the protection scope of the present invention.

What is claimed is:

1. An immunochromatographic test paper card for testing clothianidin, comprising:
   a base plate; a sample pad, a binding pad, a nitrocellulose (NC) film, and an absorption pad that are sequentially arranged on the base plate, wherein:
   the binding pad comprises a detection microsphere and a quality control microsphere thereon, wherein the detection microsphere is a fluorescent microsphere coated with a clothianidin monoclonal antibody, and the quality control microsphere is a fluorescent microsphere coated with a rabbit anti-tag protein;
   the NC film is provided with a detection line and a control line thereon, the lengths of the detection line and the control line are the same as the width of the NC film, the detection line is coated with a clothianidin antigen, and the quality control line is coated with an anti-rabbit antibody;
   a first clamping part is arranged at one end of the sample pad; a second clamping part and a third clamping part are respectively arranged at two ends of the binding pad;
   a fourth clamping part is arranged at one end of the NC film, and the other end of the NC film is joined with the absorption pad; and the first clamping part, the second clamping part, the third clamping part and the fourth clamping part are all of semi-arc structures; the first clamping part and the second clamping part fit to each other, and the third clamping part and the fourth clamping part fit to each other; wherein, the first clamping part and the sample pad; the second clamping part, the third clamping part and the binding pad; and the fourth clamping part and the NC film are all integrally formed structures.

2. The immunochromatographic test paper card for testing clothianidin according to claim 1, wherein an upper side surface of the other end of the sample pad is provided with several groove-shaped structures.

3. The immunochromatographic test paper card for testing clothianidin according to claim 2, wherein the base plate is provided with a first semi-arc supporting part and a second semi-arc supporting part thereon; a first supporting part is positioned at a lower side of the second clamping part; and the second supporting part is positioned at a lower side of the third clamping part.

4. The immunochromatographic test paper card for testing clothianidin according to claim 3, wherein a joint portion between the NC film and the absorption pad is corrugated, wherein a concave-convex alternate structure is presented on an end surface of the NC film; a concave-convex alternate structure is presented on an end surface of the absorption pad; and the NC film and the absorption pad are embedded and engaged with each other.

5. The immunochromatographic test paper card for testing clothianidin according to claim 4, wherein the base plate is provided with a third semi-arc supporting part and a fourth semi-arc supporting part thereon; a first raised buffer part is arranged adjacent to an end surface of the absorption pad; a second raised buffer part is arranged at the other end surface of the absorption pad; the third semi-arc supporting part is arranged on the base plate below the first raised buffer part, and the fourth semi-arc supporting part is arranged on the base plate below the second raised buffer part.

6. The immunochromatographic test paper card for testing clothianidin according to claim 5, wherein the fitting parts of the first clamping part and the second clamping part, the third clamping part and the fourth clamping part are engaged into each other through the concave-convex alternate structure.

7. The immunochromatographic test paper card for testing clothianidin according to claim 6, wherein an upper side surface of the second clamping part is provided with a projection, and the projection has a width smaller than the width of a second clamping part; the lower side surface of the first clamping part is provided with a strip-shaped groove; and the projection is embedded in the groove.

* * * * *